United States Patent [19]
Turk et al.

[11] Patent Number: 5,562,727
[45] Date of Patent: Oct. 8, 1996

[54] INTRALUMINAL GRAFT AND METHOD FOR INSERTION THEREOF

[75] Inventors: Rodney E. Turk, West Bloomfield; Timothy S. Dickerson, Brooklyn; Jeffery T. Gotro, Ann Arbor, all of Mich.

[73] Assignee: Aeroquip Corporation, Maumee, Ohio

[21] Appl. No.: 319,965

[22] Filed: Oct. 7, 1994

[51] Int. Cl.⁶ .................... A61F 2/06; A61F 2/04
[52] U.S. Cl. .................................. 623/1; 623/12
[58] Field of Search .................... 623/1, 11, 12; 606/194, 195; 600/36

[56] References Cited

U.S. PATENT DOCUMENTS

| | | |
|---|---|---|
| 4,195,623 | 4/1980 | Zeff et al. . |
| 4,195,637 | 4/1980 | Gruntzig et al. . |
| 4,264,990 | 5/1981 | Hamas .................................. 623/8 |
| 4,271,839 | 6/1981 | Fogarty et al. . |
| 4,386,601 | 6/1983 | Trick . |
| 4,508,112 | 4/1985 | Seeler . |
| 4,577,631 | 3/1986 | Kreamer . |
| 4,649,914 | 3/1987 | Kowalewski . |
| 4,733,665 | 3/1988 | Palmaz . |
| 4,739,762 | 4/1988 | Palmaz . |
| 4,740,207 | 4/1988 | Kreamer . |
| 4,762,130 | 8/1988 | Fogarty et al. . |
| 4,769,029 | 9/1988 | Patel . |
| 4,774,949 | 10/1988 | Fogarty . |
| 4,776,337 | 10/1988 | Palmaz . |
| 4,787,899 | 11/1988 | Lazarus . |
| 4,793,348 | 12/1988 | Palmaz . |
| 4,795,458 | 1/1989 | Regan . |
| 4,877,025 | 10/1989 | Hanson . |
| 4,955,895 | 9/1990 | Sugiyama et al. . |
| 5,156,620 | 10/1992 | Pigott .................................. 606/194 |
| 5,192,311 | 3/1993 | King et al. .......................... 623/1 |

*Primary Examiner*—Debra S. Brittingham
*Attorney, Agent, or Firm*—Emch, Schaffer, Schaub & Porcello

[57] ABSTRACT

An intraluminal graft/stent includes a hollow tubular member with inner and outer wall members defining a cavity in which is positioned a time-delay, heat-activated material partially filling the cavity. Upon implantation of the graft/stent in the blood vessel to be repaired, the time-delay, heat-activated material will foam and expand to completely fill the cavity causing the outer wall to sealingly engage the interior wall of the blood vessel. The inner wall, upon expansion, provides a conduit for the flow of blood. Under one embodiment, a flexible support member encircles the outer wall member and, by virtue of its shorter length and smaller cross-sectional size than the outer wall member causes enlarged cuffs to be formed at opposing ends of the graft/stent upon completion of expansion of the time-delay, heat-activated material.

10 Claims, 3 Drawing Sheets

INTRALUMINAL GRAFT AND METHOD FOR INSERTION THEREOF

BACKGROUND ART

The present invention relates to a new and novel intraluminal graft/stent and for a method of implantation and is more specifically related to an intraluminal graft/stent which is particularly well suited for non-invasive treatment of aortic aneurysms and diseased blood vessels.

U.S. Pat. No. 5,156,620, incorporated herein by reference, discloses an intraluminal graft/stent having inner and outer layers or tubes of resilient material suitable for implantation in a blood vessel. According to the invention described in U.S. Pat. No. 5,156,620, inner and outer tubes of flexible, semi-rigid material suitable for insertion in a blood vessel for long periods of time are joined together at their opposite ends such that a space or chamber is defined between the inner tube and the outer tube when such tubes are in their expanded position. The unit defined by such joined together inner and outer tubes is collapsed to a size permitting its insertion via the femoral artery of the patient. Using an expandable catheter, the unit is then inserted via the femoral artery to the site of the blood vessel to be repaired. When thus properly positioned, the catheter expands the unit. Suitable plastic material is then introduced into the chamber and, upon filling, the intraluminal graft is firmly engaged at its opposite end to the interior wall of the blood vessel.

DISCLOSURE OF THE INVENTION

Under the present invention an intraluminal graft/stent includes (1) a hollow tubular member having inner and outer walls of resilient material joined together and cooperating to define a cavity and (2) a time-delay, heat-activated material partially filling the cavity prior to insertion of the hollow tubular member into the lumen or blood vessel to be repaired. The partially filled tubular member is collapsed around a catheter and is directed through blood vessels to become properly positioned at the site requiring repair prior to the time required to activate the time-delay, heat-activated material. The time-delay, heat-activated material will, at a point in time following positioning at the site to be repaired, expand to fill the cavity and cause the outer wall to be urged snugly against the inner wall of the blood vessel to be repaired on opposite ends of the repair site.

Under one embodiment, a flexible support member snugly encircles the outer wall member from a first area spaced from one end of the hollow tubular member to a second area spaced from the opposite end of the hollow tubular member. The diameter of the flexible support member is smaller than the diameter of the unrestrained portions of the outer wall member. This results in the intraluminal graft member, upon expansion of the time-delay, heat-activated material having enlarged ends extending radially outwardly from the support member. The enlarged ends become sealingly engaged to the interior wall of the blood vessel.

The method for inserting the intraluminal graft/stent includes providing the hollow tubular member with time-delay, heat-activated material partially filling the cavity and, thereafter, positioning such member into the blood vessel and permitting the time-delay, heat-activated material to expand to fill the cavity such that opposing ends of the outer wall member sealingly engage the interior wall of the blood vessel to be repaired. The properties of the time-delay heat-activated material are such that it may be introduced into the cavity long before insertion of the stent in the patient simply by maintaining the temperature below the temperature required to activate such material. Thus, the stent can be manufactured under optimum conditions at a manufacturing facility remote from the hospital and refrigerated for extended periods of time prior to use.

BEST MODE OF CARRYING OUT INVENTION

Figure 1:
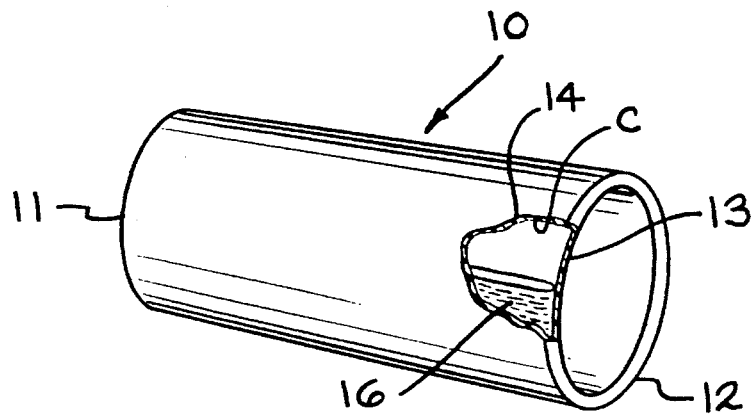
FIG. 1 is a perspective view showing one embodiment the intraluminal graft/stent of the present invention and showing time-delay, heat-activated material prior to its activation partially filling the cavity between the inner and outer layers.

Referring now to FIG. 1, there is shown an intraluminal graft/stent 10 extending from a first end 11 to a second end 12. The stent includes an inner layer 13 and an outer layer 14 which are joined together at the ends 11 and 12. The inner layer 13 and outer layer 14 are formed of a flexible, semi-rigid material such as a polytetrafluoroethylene or suitable biocompatible material. Dacron® and Gore-tex® are two well-known types of material which could be used for the inner and outer layers 13 and 14. The outer layer 14, when in its uncollapsed, expanded position shown in FIG. 1 has a larger cross-sectional size than the inner layer 13 when similarly non-collapsed and expanded and is spaced therefrom and cooperates therewith to define a chamber or cavity C therebetween. Partially filling the cavity C is a time-delay, heat activatable polymer 16 which is sealed in the cavity C after introduction therein. A suitable time-delay, heat activated polymer includes a polyurethane sold by BASF under the name BASF Pluracol P series cured with a delayed action catalyst or a silicone sold by Dow Corning under the name Silastic Liquid Silicone rubber cured with a platinum hydrosilation catalyst.

The intraluminal graft/stent 10, following introduction of the time-delay, heat-activated polymer 16, is refrigerated so that the polymer remains dormant until such time as the graft/stent is implanted in the blood vessel to be repaired.

Implantation may be performed using a balloon catheter as is well-known in the art. Following implantation to the desired site of the blood vessel to be repaired and heating of the intraluminal stent/graft 10 to body temperature, the polymer 16, after a slight delay in time depending upon the precise formulation of material used, will expand by foaming to fill the cavity C causing portions of the the outer layer 14 adjacent the ends 11 and 12 to sealingly engage the interior wall of the blood vessel to be repaired.

Figure 2:
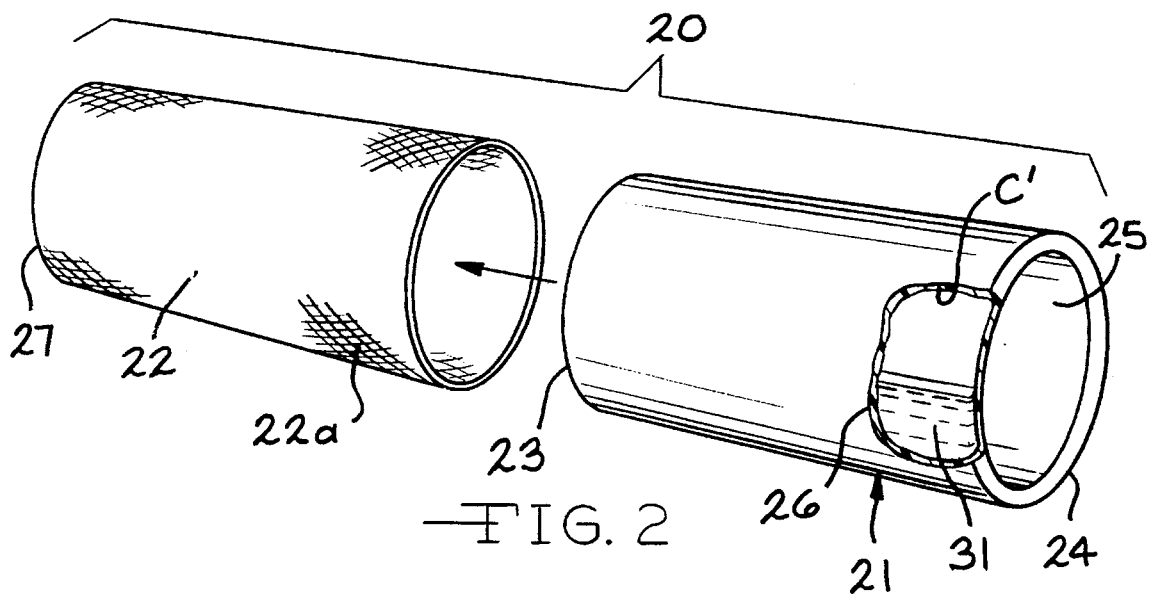
FIG. 2 is an exploded perspective view of another embodiment of the present invention in which a support member is utilized in combination with a hollow tubular member having inner and outer walls.
Figure 3:
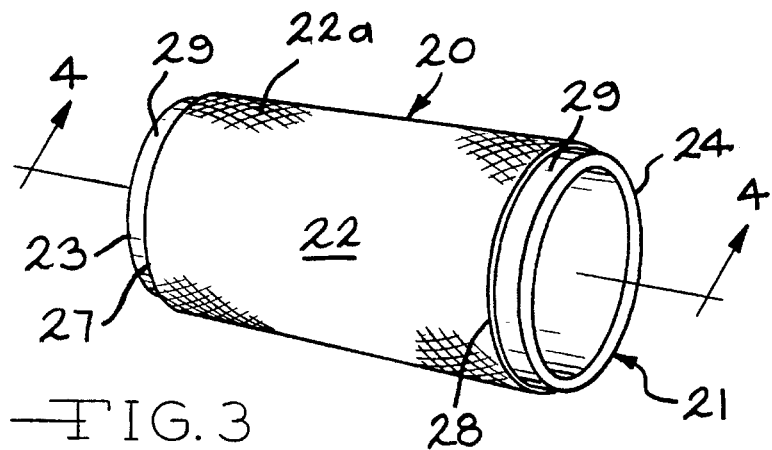
FIG. 3 is a perspective view of the intraluminal graft member of FIG. 2 showing the flexible support member snugly positioned over the outer wall member of the hollow tubular member.
Figure 4:
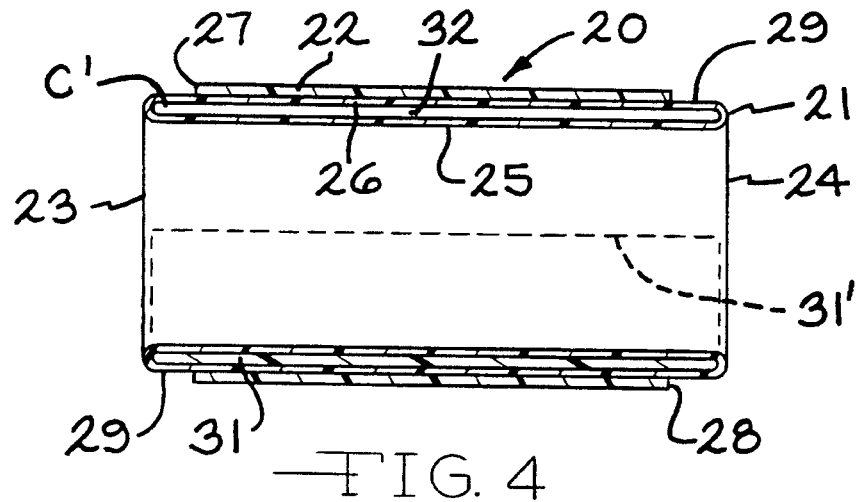
FIG. 4 is a sectional view taken along line 4—4 of FIG. 3 prior to activation of the time-delay, heat-activated material.

Referring now to FIGS. 2–4, there is shown a modified embodiment in which there is provided an intraluminal graft/stent 20 comprising a hollow tubular member 21 and a flexible support member 22 encircling and snugly engaging the tubular member 21. The tubular member 21 extends from a first end 23 to a second end 24 and includes an inner layer 25 and an outer layer 26 joined to the inner layer 25 at the first and second ends 23 and 24. As in the previous embodiment of FIG. 1, the outer layer 26, when in its non-collapsed, expanded position has a cross-sectional size greater than that of the inner layer 25 and cooperates therewith to define a cavity C' which is partially filled with a time-delay, heat activated polymer 31.

The flexible support member 22 may be formed of similar material as that of the inner and outer layers 25 and 26; however such flexible support member 22 preferably includes braided strands 22a to give the support member 22 greater resistance to expansion than the outer layer 14. As may be seen particularly in FIGS. 3 and 4, the flexible support member 22 extends from a first end 27 which is spaced from the first end 23 of the tubular member 21 to a second end 28 which is spaced from the second end 24 of the tubular member 21. Thus, the intraluminal graft/stent 20 of the embodiment of FIGS. 2–4 has what may be characterized as cuff forming portions 29 in the areas adjacent the first end 23 and second end 24, respectively.

FIG. 4 shows the intraluminal graft/stent 20 as it would look if the inner layer 25 and outer layer 26 were fully expanded but prior to insertion in a blood vessel and prior to activation of the time-delay, heat activated polymer. Thus, FIG. 4 shows the time-delay, heat activated polymer 31 in section only in the lower portion of the tubular member 21 and an air gap 32 between the inner layer 25 and outer layer 26 at the upper portion of FIG. 4. Assuming the time-delay, heat-activated polymer 31 prior to activation occupied about one-half of the cavity C', it would extend in the cavity C' to about the line designated 31'. The reason for this is that prior to activation of the time-delay heat activated polymer 31, the cavity C' between the inner layer 25 and outer layer 26 is only partially filled with such time-delay, heat activated polymer. Although FIG. 4 was drawn to show the intraluminal graft/stent 20 as it would look if the inner layer 25 and outer layer 26 were fully expanded, it will be appreciated that preparatory to insertion in the body, it will be collapsed to reduce the size as shown in FIG. 5.

Referring now to FIGS. 5–8, there is shown the procedure and apparatus utilized in positioning the intraluminal graft/stent 20 in a blood vessel V. As may be seen in FIGS. 6–8, a blood vessel V is shown as having a diseased/weakened area 30 which has ballooned outwardly and is in danger of rupturing. An expandable angioplasty balloon-type catheter 40 of a type well-known in the art may be utilized to position the intraluminal graft/stent 20 to the weakened portion 30 of the blood vessel V. Balloon catheters are well-known in the art and will, therefore, not be described in detail. The balloon catheter 40 is shown schematically in FIGS. 5–7 and may include a flexible balloon 41 mounted on a hollow guide wire 42. The hollow guide wire 42 has a plurality of apertures 43. The balloon 41 is sealingly engaged to the guide wire 42 at opposing ends 44 and 45 and may be expanded from a collapsed position shown in FIGS. 5 and 6 to an expanded position shown in FIG. 7 by the introduction of pressured fluid through apertures 43.

Sometime prior to time the intraluminal graft/stent is to be introduced into the blood vessel of the patient during the surgical procedure, the intraluminal graft/stent is removed from refrigeration and permitted to warm to a temperature approximating room temperature and possibly as high as about body temperature. Although this may cause the polymer 31 to reach the "activating temperature" the fact that it has a time-delay feature permits the graft/stent 20 to be properly positioned in the blood vessel V prior to initiation of foaming/expansion of such polymer.

Figure 5:
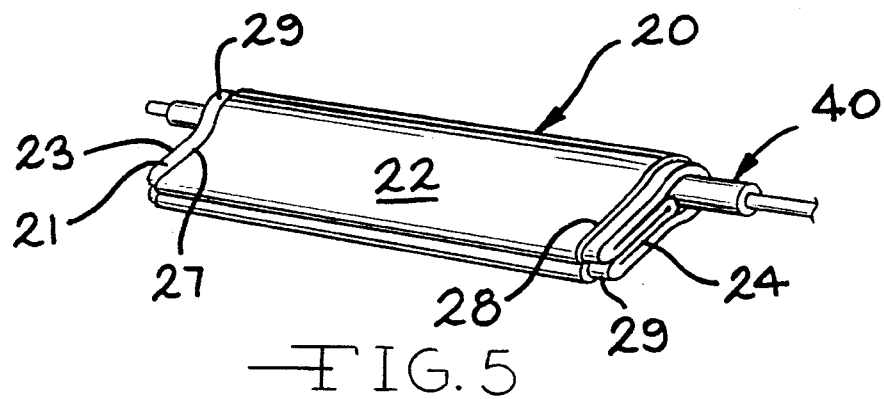
FIG. 5 is a perspective view showing the intraluminal graft member of the embodiment of FIG. 2 collapsed around a catheter and ready for positioning in a blood vessel.
Figure 8:
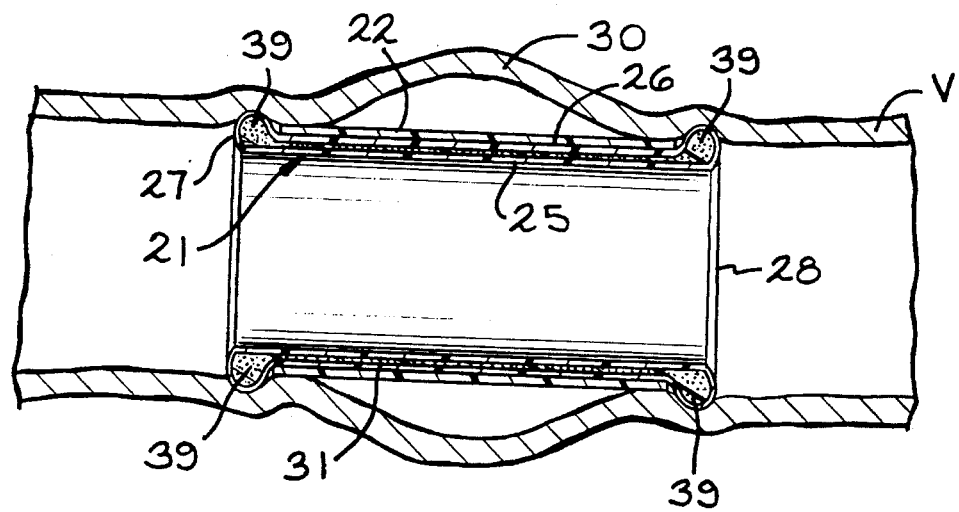
FIG. 8 is a sectional view showing the intraluminal graft/stent of FIG. 2 following full expansion of the time-delay activated material within the cavity with opposing ends of the stent engaged to the interior wall of the blood vessel.

The intraluminal graft/stent 20 is collapsed around the catheter 40 as shown in FIG. 5 and is then fed through the femoral artery or other suitable entrance point of the body to the blood vessel V and positioned such that it spans of the weakened portion 30 and some distance therebeyond (FIG. 6) so that upon final placement as shown in FIG. 8, the intraluminal stent/graft will be in contact with healthy tissue of the blood vessel V.

Figure 6:
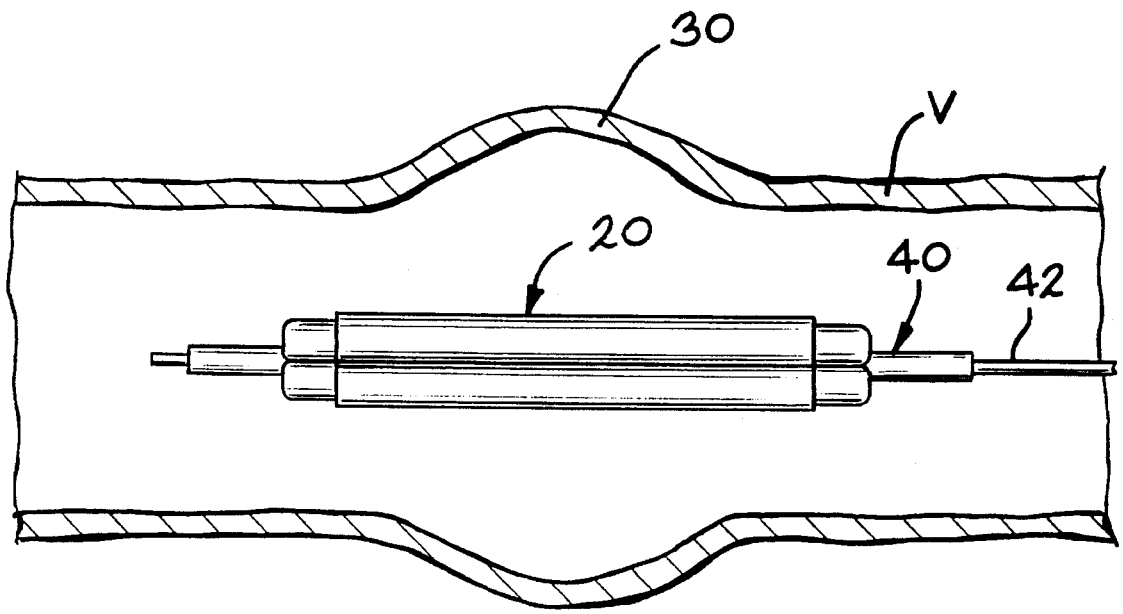
FIG. 6 is a sectional view showing a blood vessel with the collapsed intraluminal graft/stent spanning the site to be repaired.
Figure 7:
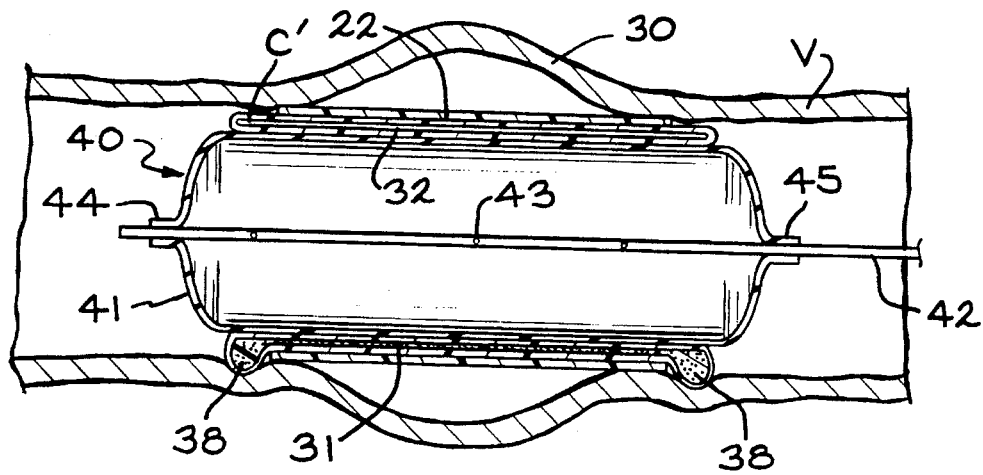
FIG. 7 is a view showing the intraluminal graft/stent expanded on the catheter.

FIG. 6 shows the catheter 40 with the collapsed intraluminal graft/stent 20 in position for expansion from the collapsed position and activation of the time-delay, heat activated polymer 31. Pressurized air or other fluid is then introduced through the apertures 43 to expand the balloon 41 of the catheter 40 to the full extent permitted by the inner layer 25 as shown in FIG. 7. Since the time-delay, heat-activated polymer 31 has not yet become activated, it occupies only the lower portion (as viewed in FIG. 7) of the cavity C. The presence of the flexible support member 22 causes the polymer 31 to be forced to the ends 38 of the cavity C'. When maintained in this position for the length of time required by the specific time-delay, heat activated polymer 31, such polymer will become activated and foam to expand within and completely fill the remaining portions of the cavity C'. As can be seen in FIGS. 7 and 8, such expansion will cause the time-delay, heat activated polymer 31 to flow to the respective first and second ends 23 and 24 and bulge the respective portions of the tubular member 21 between the first end 23 of the tubular member and first end 27 of the flexible support member 22 and between the second end 24 of the tubular member 21 and the second end 28 of the flexible support member outwardly to form cuffs 39 which snugly engage and become joined to the interior wall of the blood vessel V.

Figure 9:
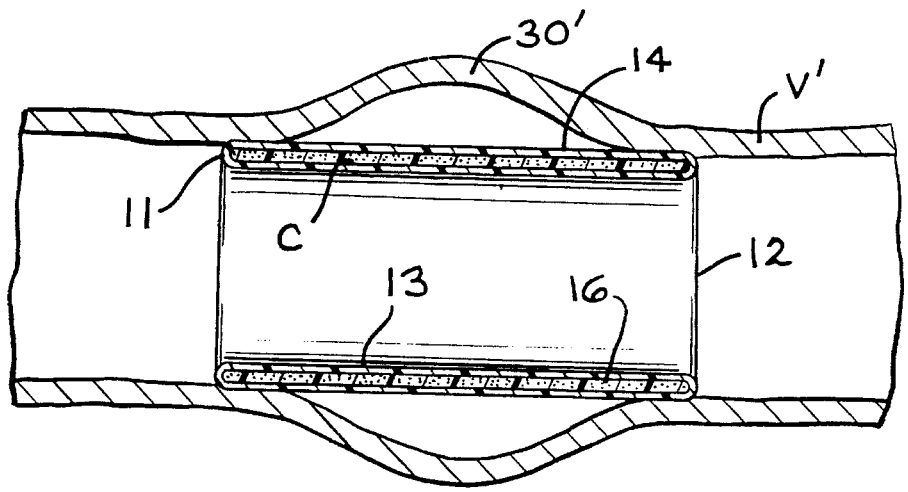
FIG. 9 is a view similar to FIG. 8 showing the embodiment of FIG. 1 fully implanted in a blood vessel.

As will be appreciated, and as can be seen in FIG. 9, although the intraluminal stent/graft 10 of the embodiment of FIG. 1 does not have cuffs 39 as shown in the embodiment of FIGS. 2–8, it also snugly engages the interior wall of the blood vessel V upon expansion by the balloon catheter 40 and expansion of the time-delay, heat activated polymer 16 contained in its cavity C.

Many modifications to the present invention will become readily apparent to those skilled in the art. Accordingly, the present invention should be limited in scope only by the scope of the claims appended hereto.

We claim:

1. An intraluminal graft member suitable for implantation in a blood vessel comprising:
  (a) a hollow tubular member extending from a first end to a second end, said tubular member having:
   (i) an inner wall member of resilient material,
   (ii) an outer wall member of resilient material encircling said inner wall member, (iii) means adjacent said first end and said second end for joining said inner wall member and said outer wall member and cooperating therewith to define a cavity, and (iv) a time-delay, heat-activated material partially filling said cavity said material being activated after implantation upon reaching body temperature; said tubular member being collapsible to a reduced cross-sectional size following placement but before activation of said time-delay, heat-activated material in said cavity and expandable to a larger cross-sectional size upon activation and expansion of said time-delay, heat-activated material, said inner wall member, when at said larger cross-sectional size, defining a passageway for transmission of blood.

2. An intraluminal graft member according to claim 1 further including a flexible support member encircling said outer wall member from a first area spaced from said first end to a second area spaced from said second end.

3. An intraluminal graft member according to claim 2, wherein said outer wall member between (a) said first area and said first end and (b) said second area and said second end define, when said tubular member is at said larger cross-sectional size, first and second abutments, respectively, each having a cross-sectional size greater than the cross-sectional size of said flexible support member.

4. The intraluminal graft member according to claims 1, 2 or 3, wherein said time-delay, heat-activated material is a polymer selected from the group consisting of polyurethane and silicone.

5. An intraluminal graft member comprising:

(a) a hollow tubular member formed of flexible material movable from a collapsed to an expanded position, said tubular member including an inner member and an outer member and a cavity therebetween and, when in the expanded position, said inner member defining a passageway for the flow of fluids; and (b) a time-delay, heat-activated material in said cavity, said time-delay, heat-activated material, said material being activatable upon time-delay, heat-activated material being activated after implantation reaching body temperature and partially filling said cavity before activation and substantially completely filling said cavity after activation.

6. An intraluminal graft member comprising:

(a) a hollow tubular member extending from a first end to a second end and formed of flexible material movable from a collapsed to an expanded position, said tubular member including an inner member and an outer member and a cavity therebetween and, when in the expanded position, said inner member defining a passageway for the flow of fluids;

(b) a time-delay, heat-activated material in said cavity, said time-delay, heat-activated material, said material being activated after implantation upon reaching body temperature and partially filling said cavity before activation and substantially completely filling said cavity after activation; and (c) a flexible support member encircling said hollow tubular member in contact with said outer member, said flexible support member having a length shorter than the distance between said first end and said second end and providing substantially unyielding support against radial enlargement of the contacted portion of said tubular member, each of said first end and said second end extending beyond said flexible support member, said tubular member having a first portion adjacent said first end and a second portion adjacent said second end which define when said tubular member is in said expanded position, first and second enlargements, each having a cross-sectional size greater than the cross-sectional size of said flexible support member.

7. An intraluminal graft member according to claims 5 or 6, wherein said time-delay, heat-activated material is a polymer selected from the group consisting of polyurethane and silicone.

8. A method for implanting an intraluminal stent in a blood vessel comprising:

(a) providing a stent deformable between a collapsed position and an expanded position and extending from a first end to a second end, said stent including:
 (i) an inner wall member of resilient material,
 (ii) an outer wall member of resilient material encircling said inner wall member,
 (iii) means adjacent said first end and said second end for joining inner wall member and said outer wall member and cooperating therewith to define a cavity, and
 (iv) a time delay, heat-activated material is activated after implantation reaching body temperature partially filling said cavity;

(b) collapsing said stent to a reduced cross-sectional size;

(c) positioning said collapsed stent into said blood vessel;

(d) expanding said inner wall member; and (e) maintaining said stent in said position while said time-delay, heat-activated material expands within said cavity to engage portions of said outer wall member adjacent said first end and said second end to said blood vessel.

9. A method for implanting an intraluminal stent in a blood vessel comprising:

(a) providing a stent deformable between a collapsed position and an expanded position and extending from a first end to a second end, said stent including:
 (i) an inner wall member of resilient material,
 (ii) an outer wall member of resilient material encircling said inner wall member,
 (iii) means adjacent said first end and said second end for joining inner wall member and said outer wall member and cooperating therewith to define a cavity,
 (iv) a time-delay, heat-activated material is activated after implantation upon reaching body temperature partially filling said cavity; and
 (v) a flexible support member encircling said outer wall member from a first area spaced from said first end to a second area spaced from said second end, (b) collapsing said stent to a reduced cross-sectional size;

(c) positioning said collapsed stent into said blood vessel;

(d) expanding said inner wall while said stent is positioned within said blood vessel; and (e) maintaining said stent in said position while said time-delay, heat-activated material expands within said cavity to form a first cuff between said first end and said flexible support member and a second cuff between said second end and said flexible support member said first and second cuffs extending laterally beyond said support member and engaging said blood vessel.

10. The method according to claims 8 or 9, wherein said time-delay, heat-activated material is a member of the group consisting of polyurethane and silicone.

* * * * *